United States Patent [19]

Lesyna et al.

[11] Patent Number: 5,260,581
[45] Date of Patent: Nov. 9, 1993

[54] METHOD OF TREATMENT ROOM SELECTION VERIFICATION IN A RADIATION BEAM THERAPY SYSTEM

[75] Inventors: David A. Lesyna; Jon W. Slater, both of Redlands, Calif.

[73] Assignee: Loma Linda University Medical Center, Loma Linda, Calif.

[21] Appl. No.: 846,531

[22] Filed: Mar. 4, 1992

[51] Int. Cl.5 .............................................. G22G 1/10
[52] U.S. Cl. .................................. 250/492.3; 250/398
[58] Field of Search ................ 250/492.3, 492.1, 398; 328/233, 234, 235; 364/413.14, 413.15

[56] References Cited

U.S. PATENT DOCUMENTS 4,870,287 9/1989 Cole et al. ......................... 250/492.3

Primary Examiner—Paul M. Dzierzynski
Assistant Examiner—Kiet T. Nguyen
Attorney, Agent, or Firm—Robert R. Meads

[57] ABSTRACT

The present invention is directed to a method of treatment room selection verification in a radiation beam therapy system. The method compares treatment room beam request signals with a beam path configuration signal from a switchyard which controls the path of beam travel from an accelerator to one of the treatment rooms. Upon agreement of the request and beam path signals, beam transport to a selected treatment is authorized.

13 Claims, 6 Drawing Sheets

METHOD OF TREATMENT ROOM SELECTION VERIFICATION IN A RADIATION BEAM THERAPY SYSTEM

BACKGROUND OF INVENTION

The present invention relates to a method of treatment room selection verification particularly useful in a cancer therapy system as described in U.S. Pat. No. 4,870,287, assigned to the assignee of the present invention, the Loma Linda University Medical Center, and which is incorporated herein by this reference.

U.S. Pat. No. 4,870,287 describes a proton beam therapy system for selectively generating and transporting proton beams from a single proton source and accelerator to selected ones of a plurality of patient treatment stations. In the proton therapy system, patient safety is of prime importance. Accordingly, it is mandatory that the proton beam only be directed to the particular patient treatment station designated for patient treatment at any given time. The method of the present invention, insures that the proton beam of proper beam configuration is only directed to the properly selected treatment station.

SUMMARY OF INVENTION

The method of the present invention is particularly useful in a radiation beam therapy system comprising a radiation beam source and a beam accelerator for accelerating the beam to a selected one of a plurality of treatment rooms through a transport line called a switchyard. Basically, the method comprises the steps of generating or receiving a beam request signal from one or more of the treatment rooms and then verifying the authenticity of one of the beam request signals. Only when a beam request has been authenticated is beam transport to the verified treatment room authorized by the method of the present invention. The verification and authorization steps of the method of the present invention may comprise comparing the beam request signals with a beam path configuration signal from the switchyard indicating the current beam path settings for the switchyard from the accelerator to one of the treatment rooms and authorizing the beam transport only to the treatment room associated with the beam request signal in agreement with the beam path configuration signal. Preferably, the verification and authorization steps comprise comparing the beam request signals with beam configuration signals from the switchyard and the accelerator and authorizing beam transport only to the treatment room associated with the beam request signal in agreement with the beam configuration signals.

DETAILED DESCRIPTION OF INVENTION

Generally speaking, the treatment room selection verification method of the present invention is useful in a radiation therapy system comprising a radiation beam source and a beam accelerator for accelerating the beam and directing it to a selected one of the treatment rooms through a switchyard. Such a therapy system is illustrated in FIG. 1.

Figure 1:
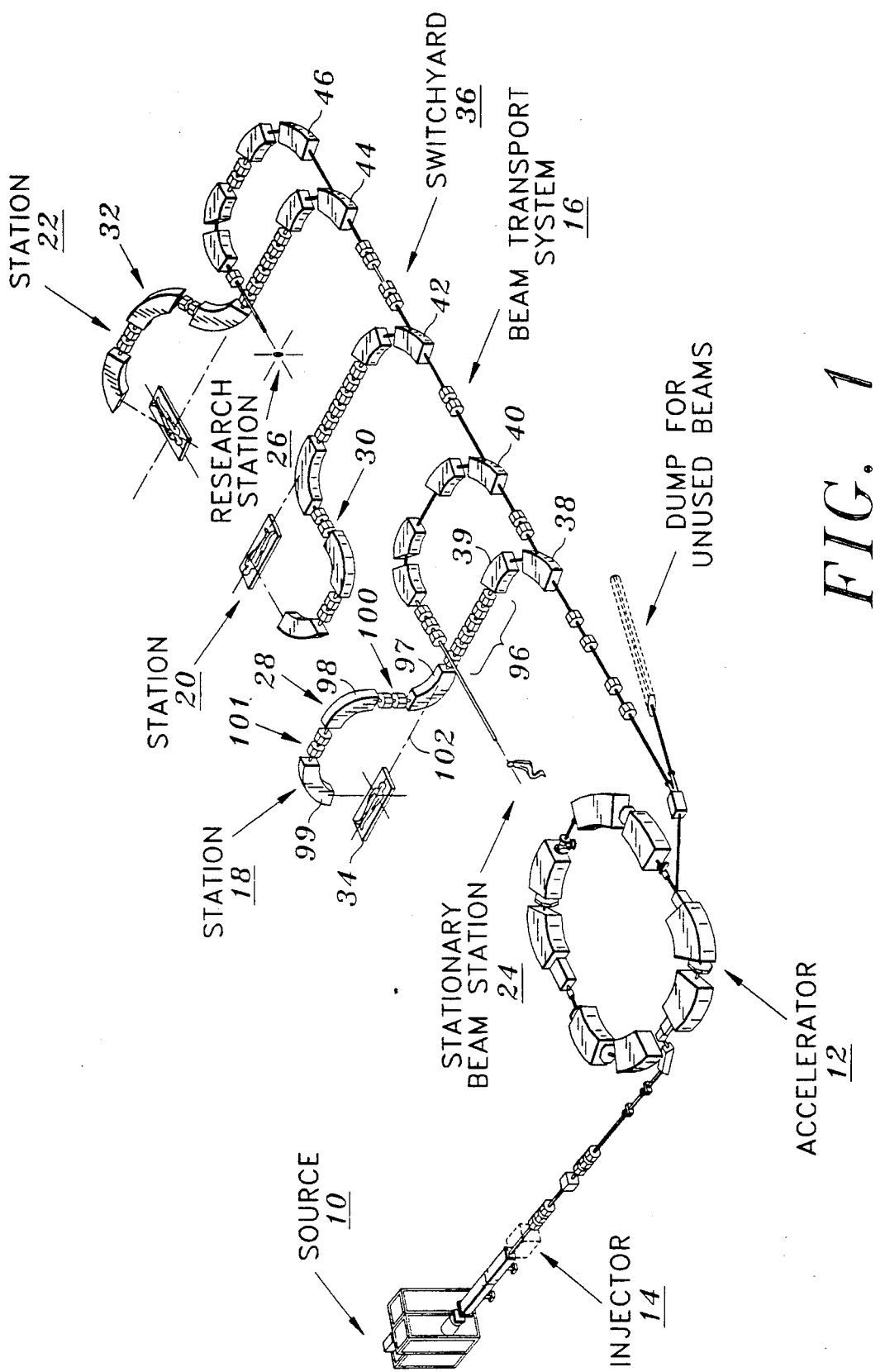
FIG. 1 is an isometric view of the structure of a proton beam therapy system in which the method of the present invention is particularly useful.
Figure 6:
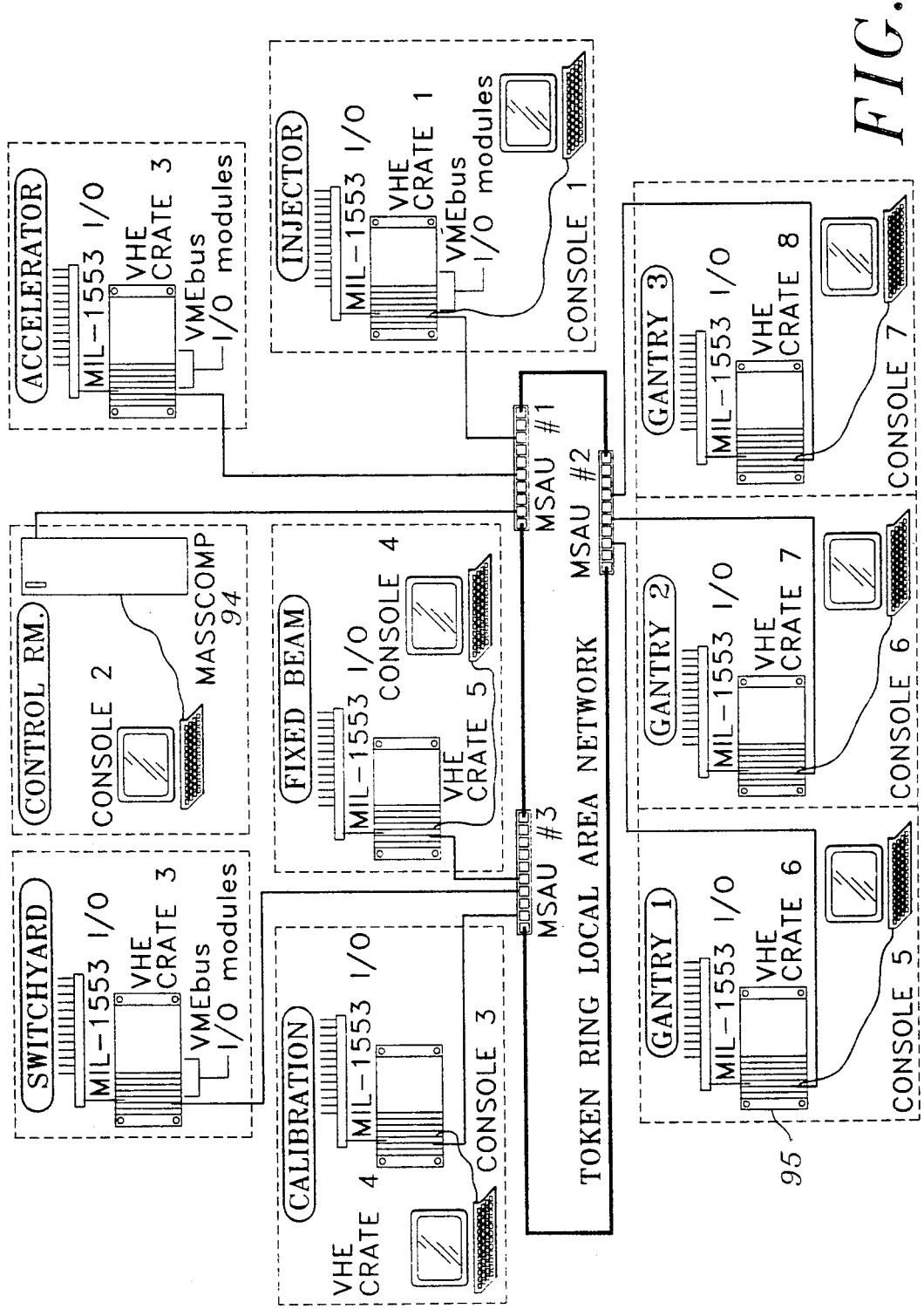
FIG. 6 is a diagram of a control system for the proton beam system of FIG. 1.

As depicted in FIG. 1, a proton beam therapy system which may incorporate the present invention comprises a proton source 10 connected to an accelerator 12 by an injector 14. The accelerator 12 accelerates the protons in a beam and via a beam transport system 16 delivers the proton beam to patients supported in fixed orientations in selected ones of a plurality of treatment stations 18, 20, 22, and 24 or to a research beam station 26. In the foregoing operation, the proton beam therapy system is under operator control via a computer control system such as illustrated in FIG. 6. At the treatment stations 18, 20 and 22, the beam transport system 16 includes gantries 28, 30 and 32 respectively, each rotatable about a different axis of rotation and carrying optics for receiving a proton beam on its axis of rotation, transporting the proton beam away from the axis of rotation and returning the proton beam on a path perpendicular to and intersecting the axis of rotation at a target isocenter within a patient supported in a fixed orientation by a patient support, such as table 34. Thus arranged, upon a rotation of the gantry, the proton beam is delivered to the target isocenter from several different angles during patient treatment.

Figure 7:
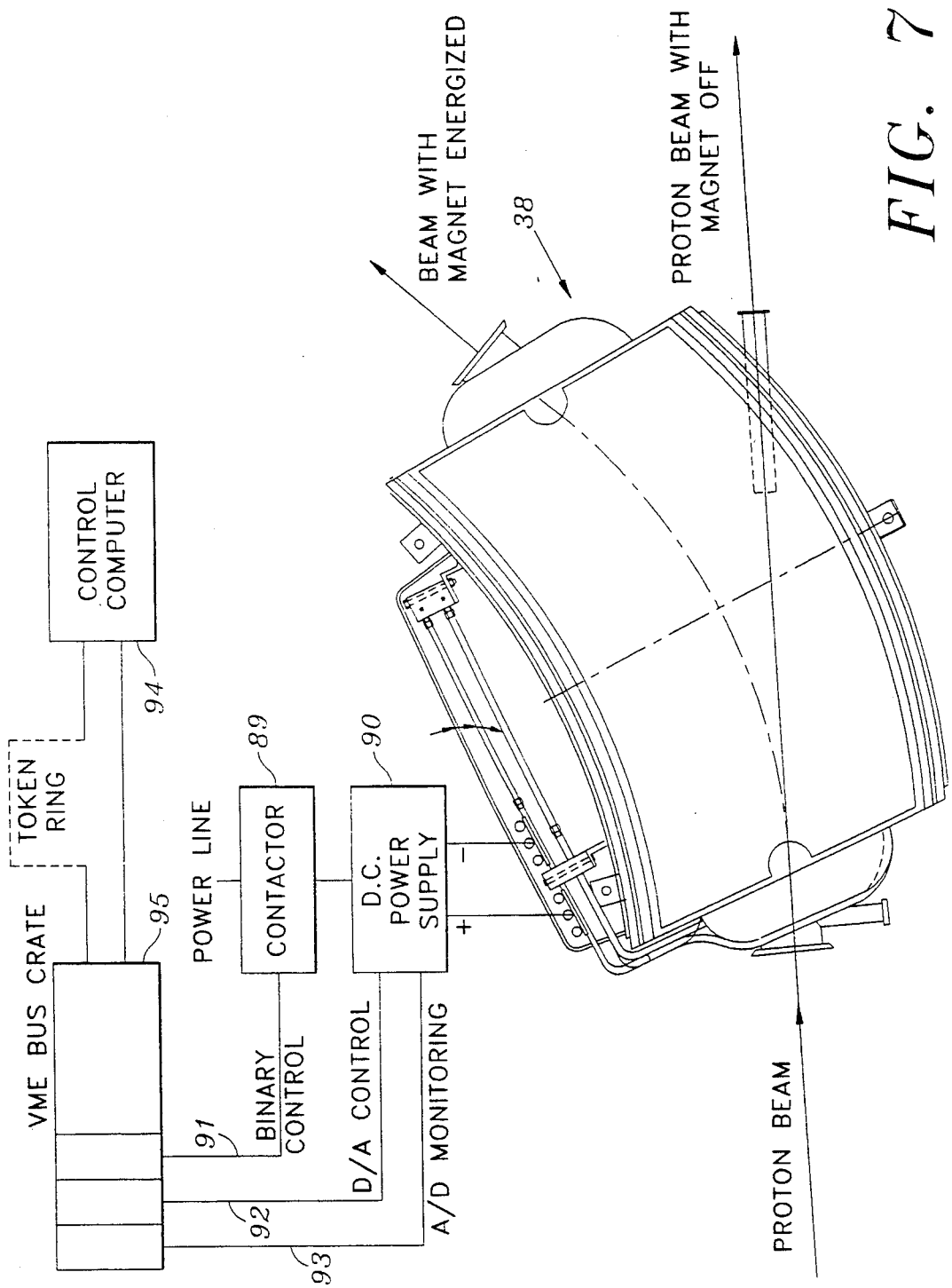
FIG. 7 is a plan view of a switching magnet and a portion of the control system of FIG. 2 for selectively controlling operation of the switching magnet.

The illustrated beam handling system 16 also includes a switchyard 36 comprising four switching magnets 38, 40, 42 and 44. Each switching magnet is characterized by two states and is electronically switchable between its two states in response to operator control of a system such as illustrated in FIG. 7. In the first state, switching magnet 38 for example will receive the proton beam from the accelerator 12 and bend and deliver the proton beam to the optics carried by the gantry 28 along the axis of rotation of gantry 28. In the second state, switching magnet 38 will pass the proton beam to the switching magnet 40 which in its first state will bend and deliver the proton beam to components in the beam stationary beam treatment station. In the second state for the switching magnet 40, it will pass the proton beam to the switching magnet 42. Like switching magnet 38, when switching magnet 42 is in its first state it will bend and direct the proton beam to the optics carried by the gantry 30 along the axis of rotation of gantry 30. In its second state, switching magnet 42 will pass the proton beam to the switching magnet 44 which in its first state will bend and deliver the beam to the optics carried by the gantry 32 along the axis of rotation of gantry 32. In its second state the switching magnet will pass the beam to a magnet 46 for bending and direction to a beam research station.

More specifically, in the construction of the illustrated proton beam therapy system, conventional components are utilized, combined, adjusted and fine-tuned according to well known ion beam transport, acceleration and focusing techniques to achieve the accelerator and injection system parameters desired and the performance specifications and parameters. See for example those listed in Appendix I, Appendix II and Tables I-VII of U.S. Pat. No. 4,870,287. As there listed, the source 10 may comprise a duoplasmatron ion source providing a 40 keV proton beam. The beam is focused by solenoidal lenses at 48 to match the beam into a radio-frequency quadrupole linear accelerator (RFQ) 50. The RFQ 50 accelerates protons to 1.7 MeV for transmission to a debuncher 52 through a quadrupole 54. The debuncher functions to reduce the momentum spread of a beam for injection into the accelerator 12 through a quadrupole 56, vertical and horizontal beam directing dipoles 58 and 60, a reverse septum magnet and injection septum 62 and final injection kicker 64. The reverse septum magnet functions to bend the injection beam 25 degrees upward while the injection septum bends the beam 20 degrees downward, the kicker bending the beam another 5 degrees downward to the injection port of the accelerator 12.

The accelerator 12 is a synchrotron containing ring dipoles, zero-gradient dipoles with edge focusing (A magnets) 66-73, vertical trim dipoles 74-77, horizontal trim dipoles 78-81, trim quadrupoles 82-85 and extraction Lambertson magnets 86. The A magnets are the main bending and focusing magnets of the synchrotron and may have the performance specifications listed in Table V of U.S. Pat. No. 4,870,287. The A magnets are built curved through a 45 degree arc. The horizontal trim dipoles 78-81 are designed to displace the beam horizontally about plus or minus 4 cm at 250 MeV. The vertical trim dipoles are similar in concept, but with an integrated strength of 0.018 T-m and a vertical displacement of plus or minus 2 cm at 250 MeV. All trim dipoles are located in the four long straight sections of the synchrotron and are individually controllable through programmable power supplies and shunts. The four trim quadrupoles 82-85 are located in the four short straight sections of the synchrotron with apertures sufficiently large to enclose beam monitors. The trim quadrupoles are also used to enclose beam monitors. The trim quadrupoles are also used to excite half-integer resonance during extraction of the beam from the synchrotron. The extraction Lambertson magnet 86 is a small aperture dc vertical dipole for bending the beam to be extracted downward out of the synchrotron.

The parameters for the acceleration system may be those set forth in Table VI and Appendix I of U.S. Pat. No. 4,870,287. To accelerate the proton beam to 250 MeV in 0.5 seconds requires an energy gain of 90 eV per turn. An RF system including an RF cavity 87 is used to accelerate the beam into extraction and to reduce the momentum spread of the extracted beam.

The parameters for beam extraction may be those set forth in Table VII and Appendix I. The beam is slow extracted from the synchrotron by horizontal half-integer resonant extraction. The tune is brought to the resonance value of 0.5 by the extraction quadrupoles 82-85. The beam is accelerated by the RF system to a electrostatic wire septum, stepped horizontally across it by the resonant amplitude growth and deflected horizontally past an iron septum in the Lambertson magnet 86. The beam is bent down 10.5 degrees by the Lambertson magnet and if not bent back to the horizontal continues straight down to a beam dump embedded in the floor housing the system. A second vertical dipole 88 similar to the Lambertson but without the septum (Dogleg Lambertson) is used to deflect the beam back to the horizontal plane for transport down the beam line to the beam transport system 16 including the switching magnets 38-44.

As previously described, the beam transport system 16 includes the switchyard 36 and the gantries 28, 30 and 32. The switchyard includes the switching magnets 38-44 and the other magnets illustrated in FIG. 1. In passing from the accelerator 12, the beam is directed through four quadrupoles to the switching magnet 38, the general function of which has been previously described. All of the switching magnets are substantially the same in structure, function and control. Accordingly, only the switch magnet 38 will be described in detail. Referring to FIG. 7, the switching magnet may be a type A' bending magnet. That is, it is similar to the previously described type A magnets with the addition of switch control features. The type A' magnet is an electromagnet configured to bend a beam of protons of a specified momentum (energy) through an angle of 45 degrees when current in a coil of the magnet is controlled to a precise current required for that momentum. When the magnet is not so energized, the protons proceed in a straight line through a hole provided in the yoke of the magnet to the next energized A' magnet. As illustrated, control of the magnet is achieved by either (i) a contractor 39 which turns on a direct current power supply 90 and concurrently sends a digitized current setting to the power supply to require the supply to regulate at a prescribed current, or (ii) opening the contractor to turn off the supply. The controls are initiated by a control computer 94 which initiates digital commands to a VME bus crate 95 (see FIG. 6). This unit then controls and monitors the operation of the power supply as indicated by the leads 91, 92 and 93.

As previously stated, the entire system as described herein is under regulation and operator control through a control system such as illustrated in FIG. 6. The illustrated control system is patterned after the system used for the Fermilab 200 MeV linac. It consists of multiple distributed microprocessor-based systems networked together and to a central MASSCOMP computer 94 using the IEEE-892.5 Local Area Network (LAN) Standard. LAN is the Token Ring protocol supported by IBM. Three 68000-based local stations are used in the control system. The MASSCOMP performs the centralized coordination of beam requests from the treatment stations in the therapy system as well as programmed beam-energy for storing operating conditions and copies of the data bases used in the local stations. The control system also provides timing pulses to the entire therapy system.

The local stations use VMEbus (IEEE-1014) hardware and Motorola 68000 processors. Each local station contains a CPU card, a network adapter and a nonvolatile RAM card to store the local data base of descriptors and parameters associated with the equipment controlled by that station. The remaining cards are analog and binary input and output interface cards that read and set parameters in the accelerator equipment. The major hardware components controlled by the local stations are the ion source 10, the injector 14, and accelerator 12 and the switching magnets.

The Token Ring is a recent network standard that is well supported by IBM and others. A twisted-pair cable forms the physical ring. Wiring concentrators provide access to the ring by the local station consoles.

While the foregoing control system will be effective in the implementation of the treatment room selection verification method of the present invention, it is to be understood that the method is not limited to such a system and to such hardware components. For example, an ETHERNET may be included instead of the token ring local area network. A plurality of interconnected or distributed computers may be included in the control room instead of the MASSCOMP. Distributed computer systems may be included in the treatment rooms and different bus configurations may be employed.

Figure 3:
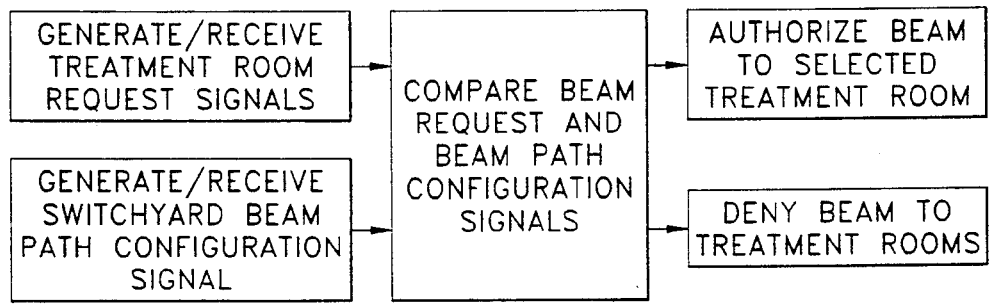
FIG. 3 is a flow diagram of a basic form of the method of the present invention.

Generally speaking, the method of the present invention in its most basic form follows the steps designated in FIG. 3. As represented, the method comprises the steps of generating or receiving treatment room beam request signals. Such signals may be generated by one or more operators in one or more of the treatment rooms. For example, referring to the system illustrated in FIG. 6, operators in the treatment rooms designated "Calibration", "Fixed Beam", and/or "Gantry 1", "Gantry 2", or "Gantry 3" may, using the illustrated consoles, generate coded signals indicative of a request for beam to the associated treatment room. As will be described hereinafter, such beam request signals, generally speaking, may be considered as including signals requesting that a beam be sent as well as a signal indicative of the configuration of the beam requested and a signal indicative of the configuration of the treatment room in readiness for receiving a beam.

In addition to the treatment room beam request signals, the method of FIG. 3 includes a step of generating and/or receiving a switchyard beam path configuration signal. Such a composite signal may be generated by detectors or monitors for the various magnets included in the switchyard. Then, as depicted in FIG. 6, such signals may be transmitted via the network to the control room for processing along with the treatment room beam request signals already described. The switchyard beam path configuration signal is indicative of and provides data corresponding to the path of the treatment beam from the accelerator through the switchyard to one of the treatment rooms.

Again, in the most basic form of the method illustrated in FIG. 3, the beam request signals from the various treatment rooms are compared with the beam path configuration signal within the selection verification system and method of the present invention. Upon the finding of an agreement between the beam path configuration signal and a treatment room beam request signal indicative of the selection of one of the treatment rooms, the method of the present invention authorizes beam to the selected treatment room. Conversely, if there is no agreement between the beam path configuration signal and any of the treatment room beam request signals, or if the beam requests from the selected treatment room includes a signal signaling a halt of beam to the selected treatment room or the aborting of beam from the accelerator to the beam dump illustrated in FIG. 1, the method of the present invention comprises a step of denying beam to the selected treatment room.

Figure 4:
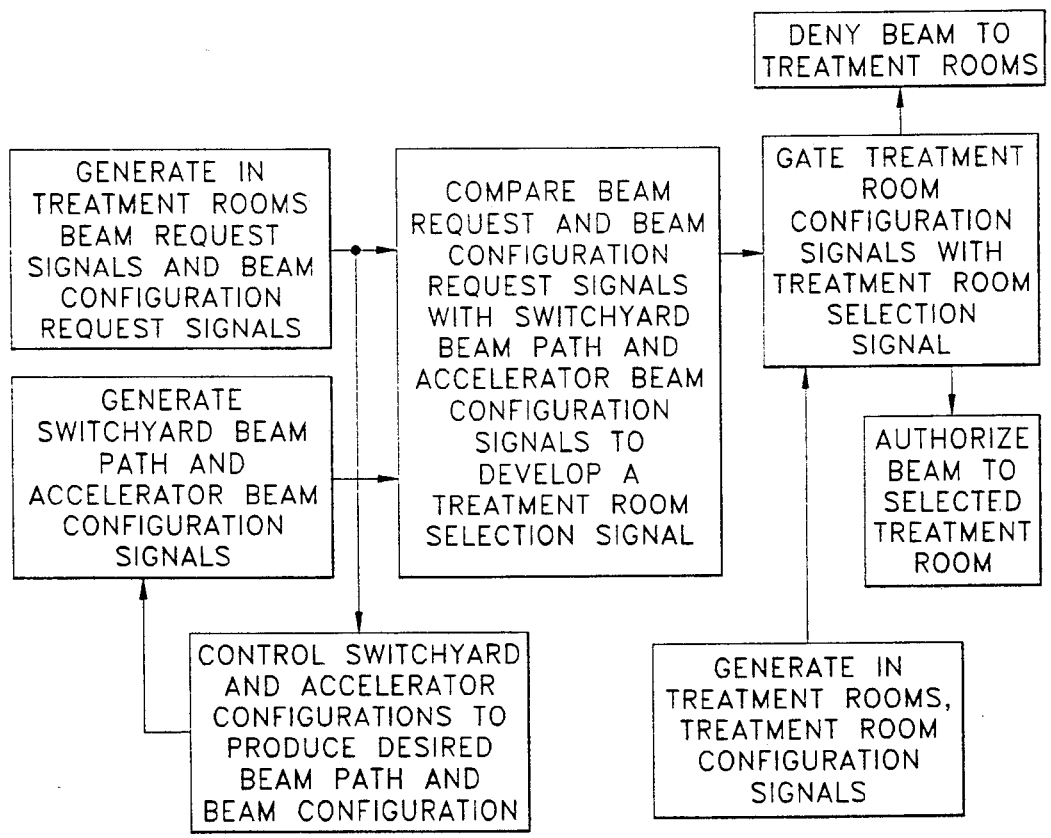
FIG. 4 is a flow diagram of a preferred form of the method of the present invention.

As previously indicated, the treatment room beam request signals may be considered as including more than just request for beam to a particular treatment room. A method including the generation and reception of a plurality of different input signals and the processing of such signals in a treatment room selection verification system and method is illustrated in FIG. 4. As there represented, a more specific method of the present invention includes a step of generating in the treatment rooms, treatment room beam request signals and beam configuration request signals. As previously described with respect to the method of FIG. 3, the treatment room beam request signal may be generated by operators in the various treatment rooms using the computer consoles illustrated in FIG. 6. Also, if it is desired that the beam reaching the treatment rooms be of a particular configuration which is under control of the operators in the treatment rooms, beam configuration request signals may also be generated by the operators in a similar manner to indicate, for example, a desired beam intensity, duration and energy.

In the method of FIG. 4, such treatment room beam request and beam configuration request signals are received and compared with switchyard beam path and accelerator beam configuration signals. The switchyard beam path configuration signal may be generated in a manner previously described with respect to the method of FIG. 3 under control of detectors or monitors for the various magnets included in the switchyard as illustrated in FIG. 1 and transmitted b the network from the switchyard to the control room as depicted in FIG. 6. In a like manner, detectors and monitors for the various magnets and controllers included in the accelerator illustrated in FIG. 1 may generate a configuration signal for the beam developed in the accelerator, such signal being transmitted from the accelerator to the control room by the network as illustrated in FIG. 6.

Within the selection verification system method of FIG. 4, the beam request and beam configuration request signals are compared with the switchyard beam path and accelerator beam configuration signals to develop a treatment room selection signal upon agreement of the signals being compared. The treatment room selection signal indicates a particular treatment room to receive beam having the requested configuration. That means that the beam request signal agrees with the switchyard beam path configuration signal and the beam configuration request agrees with the accelerator beam configuration signal for a particular treatment room.

In addition, the method illustrated in FIG. 4 includes a further step within the selection verification process namely, the gating of treatment room configuration signals with the treatment room selection signal. The treatment room configuration signals are signals which indicate the particular configuration of the treatment room in readiness for receiving a beam to treat a patient positioned in the treatment room. Such treatment room condition may indicate for example, that all x-ray sources are out of the beam line, that a range shifter block is in the beam line, that the high voltage and energy monitors are operational, etc. Similarly, the treatment room configuration signals may indicate that all conditions under which beams should be halted are not present. For example, that all doors to the treatment room that should be closed are closed. Further, such treatment room configuration signals may include signals which would trigger an aborting of the treatment beam from the accelerator. In any event, all such treatment room configuration signals are gated with the treatment room selection signal for a particular treatment room to authorize beam from the accelerator to the selected treatment room if the treatment room configuration signal does not include any so called "halt" signals or "abort" signals. If such signals are present, beam is denied to the selected treatment room in a manner previously described.

Figure 2:
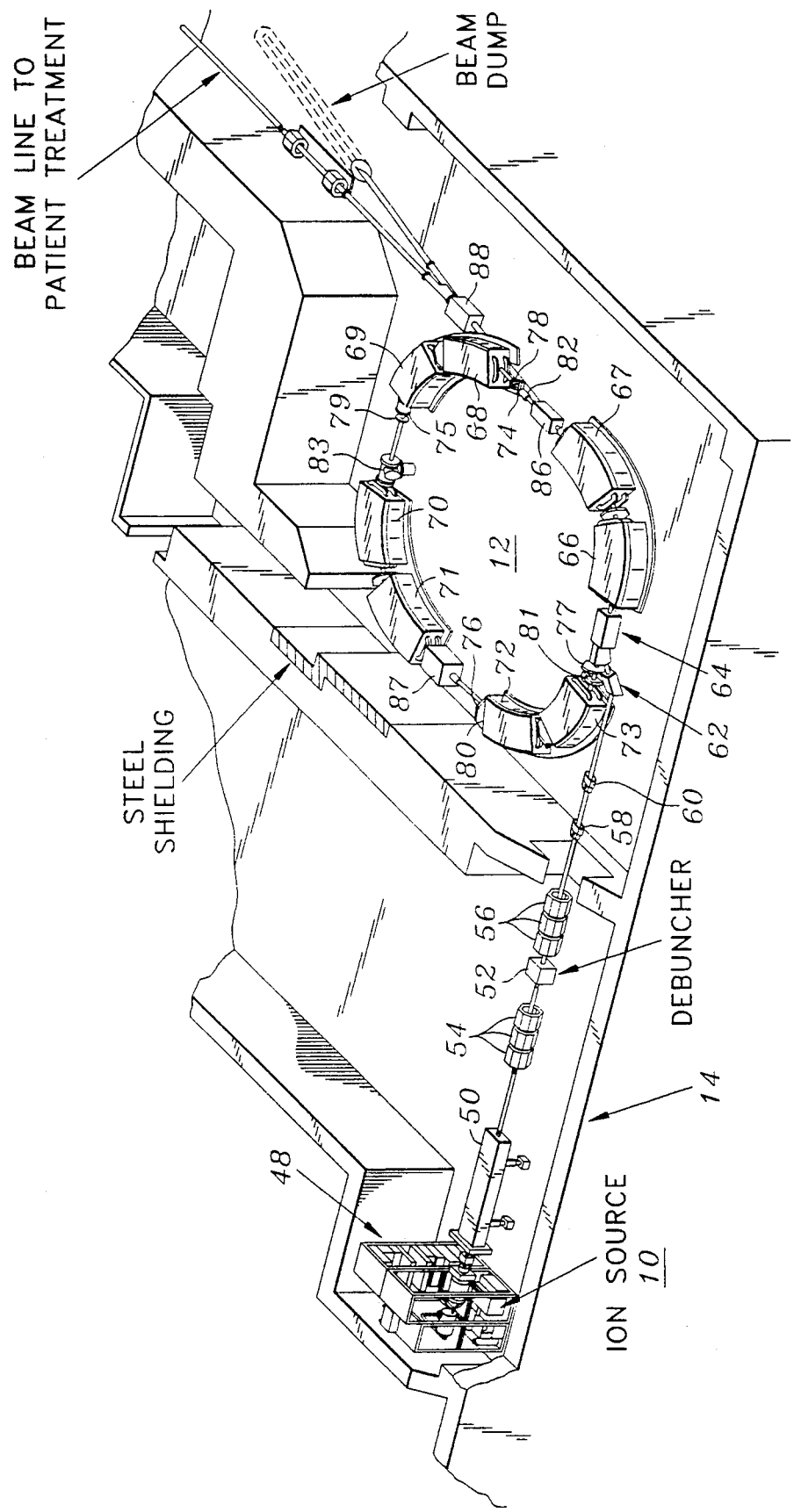
FIG. 2 is a slightly enlarged view of the proton source, injector and accelerator shown in FIG. 1.

Further, in the method depicted in FIG. 4, treatment beam configuration and beam path selection control may be affected under control of the signals from the treatment room. In particular, in the method of FIG. 4, the treatment room beam request and beam configuration signals are utilized to control the switchyard and the accelerator configurations to produce the desired beam path and beam configuration. As described in connection with FIG. 7, the beam path configuration may be controlled by signals from the control room to control the current supplied to the various magnets in the switchyard. In this regard, and in accordance with the method of the present invention illustrated in FIGS. 4 and 6, such settings of the switching magnets may be controlled from the control room by signals initiated by operators in the treatment rooms utilizing the consoles or other signal generating means. In a like manner, as described in connection with FIG. 1 and FIG. 2, the beam within the accelerator may be controlled by the various magnets included in the accelerator and their associated RF circuits and the extraction septum. Control of the current supply to such magnets will control the configuration of the beam exiting the accelerator as to energy, intensity, and duration. Such control may be affected by signals from the control room to the various accelerator magnets and may be under the control of operator generated beam configuration requests from the treatment rooms. Such steps are indicated in FIG. 4 as the step of controlling switchyard and accelerator configuration to produce desired beam path and beam configuration. As previously described, the switchyard and accelerator monitors and detectors then maybe utilized to generate the switchyard beam path and accelerator beam path configuration signals which are compared with the beam request and beam configuration request signals in the method illustrated in FIG. 4.

Figure 5:
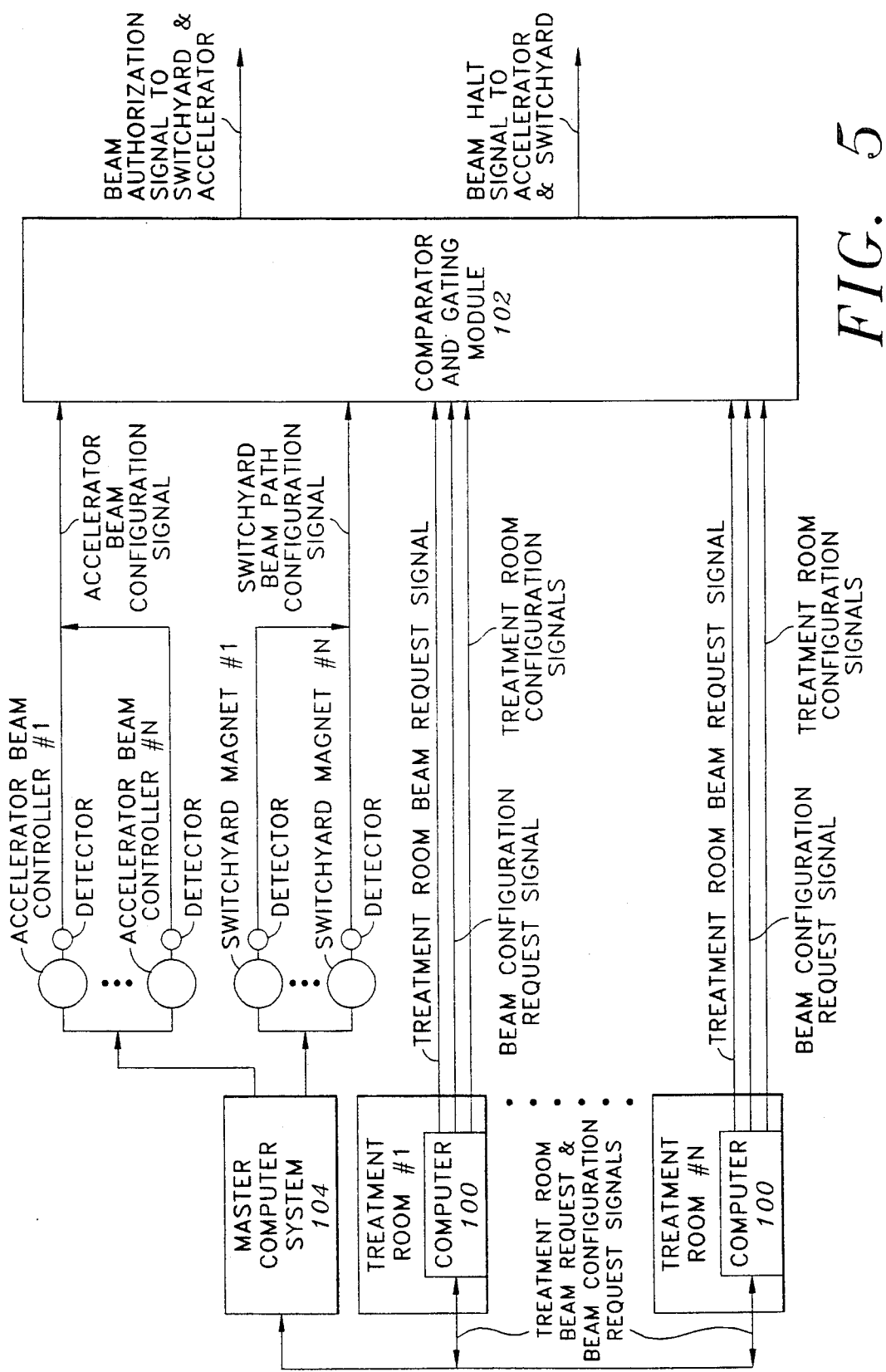
FIG. 5 is a functional block diagram of a proton therapy system substantially as illustrated in FIG. 1 and showing how the treatment room selection verification of the present invention interacts with the various treatment rooms and controllers included in the therapy system.

A system configuration providing such treatment room selection verification and control of beam path configuration and beam configuration is depicted diagrammatically in FIG. 5. As represented, the system includes a plurality of treatment rooms #1 through #N each including a computer 100 for generating a beam request signal, a beam configuration request signal, and treatment room configuration signals. Such signals are applied to a comparator and gating module 102 for processing. The beam request signals and the beam configuration request signals are also supplied to a master computer system 104, such as the MASSCOMP 94 illustrated in FIG. 6. In response to the beam request signals and beam configuration signals from each of the treatment rooms, the master computer system will determine which of the request signals, if any, will control the settings of the magnets in the switchyard and the settings of the magnets, RF circuits and the extraction septum in the accelerator to determine the beam path within the switchyard and the configuration of the beam exiting the accelerator. In the system illustrated in FIG. 5, the output of the master computer system 104 comprise setting signals for the accelerator magnets and beam configuration components represented generally as accelerator beam controllers #1 though #N, each of which has associated therewith a detector or monitor for developing a signal indicative of the status of its associated controller. Such signals combine in the comparator 102 to define an accelerator beam configuration signal indicative of the configuration of the beam generated by the accelerator for a particular setting of the various beam controllers for the accelerator.

In a like manner, the output of the master computer system 104 comprises setting signals for the various magnets included in the switchyard, indicated diagrammatically as magnets #1 through #N. Each of such magnets includes an associated detector or monitor which generates a signal indicative of the state of the magnet with which it is associated. Such signals are applied to the comparator and gating module 102 to define the switchyard path configuration signal from the switchyard. As previously described, such switchyard path configuration and beam configuration signals are compared in the comparator 102 with the request signals generated by the various treatment rooms. Upon finding an agreement between the treatment room beam request and configuration signals with the switchyard beam path configuration and accelerator beam configuration signals, the comparator develops a treatment room selection signal utilized as beam authorization signals to the switchyard and accelerator, provided that the treatment room configuration signals indicate that the treatment room is ready to receive beams with all enabling conditions being met and all beam halting and aborting conditions not being present. In the latter situation, the comparator develops a beam halting signal which denies beam from the accelerator to the switchyard and hence to any of the treatment rooms. As previously described, such treatment configuration signals are generated in each of the treatment rooms and are applied to the comparator and gating module 102 as illustrated.

The comparator and gating module 102 preferably comprises a plurality of gates and registers for comparing and processing the various signals applied as inputs. Such comparator modules are well known in the art and may be readily developed by those of ordinary skill in the art considering the design parameters set forth in this specification.

Accordingly, the present invention as described herein comprises a method for accurately verifying the selection of one of a plurality of treatment rooms to receive beam from an accelerator in accordance with an agreement between one of the beam request signals from the treatment rooms and a beam path configuration signal from the switchyard which controls the path of beam from the accelerator to the various treatment rooms. Moreover, the method preferably comprises the control of the beam path configuration through the switchyard as well as the configuration of the beam delivered to the selected treatment room by the operator control within the selected treatment room. Still further, the method of the present invention insures that through the generation of treatment room configuration signals, the beam will only be directed to the selected treatment room if the treatment is ready in all respects to receive and properly handle the beam and that there are no conditions within the treatment room which should halt the treatment beam or abort the beam from all treatment rooms.

While a particular method has been described in detail herein, it is to be appreciated that changes and modifications in the preferred method may be made without departing from the spirit of the present invention. In this regard, the present invention is to be limited in scope only by the terms of the following claims.

We claim:

1. A method of treatment room selection verification in a radiation beam therapy system comprising radiation beam source, beam accelerator, plurality of treatment rooms and a switchyard for directing accelerated beam from the accelerator to a selected one of the treatment rooms, the method comprising the steps of:
  (a) receiving a beam request signal from one or more of the treatment rooms;
  (b) verifying the authenticity of one of the beam request signals from one of the treatment rooms; and
  (c) authorizing beam transport to the one of the treatment rooms.

2. The method of claim 1 wherein steps (b) and (c) comprise comparing the beam request signal with a beam path configuration signal from the switchyard and authorizing beam transport upon agreement of the signals.

3. The method of claim 2 further comprising
  (d) denying beam transport to the selected treatment room in the absence of such verification.

4. The method of claim 1 further including generating a beam path configuration signal indicative of the beam path through the switchyard and wherein steps (b) and (c) comprise comparing the beam request signal with a beam path configuration signal and authorizing beam transport upon agreement of the signals.

5. The method of claim 3 further comprising
  (d) denying beam transport to the selected treatment room in the absence of such verification.

6. A method of treatment room selection verification in a radiation beam therapy comprising radiation beam source, beam accelerator, plurality of treatment rooms and a switchyard for directing accelerated beam from the accelerator to different selected ones of the treatment rooms, the method comprising the steps of:
  (a) receiving a plurality of input signals comprising beam requests from the treatment rooms and a beam path configuration signal from the switchyard identifying a beam path through the switchyard to one of the treatment rooms;
  (b) comparing the input signals to verify the authenticity of a request from a selected one of the treatment rooms; and
  (c) in response to such verification, allowing beam transport to the selected treatment room.

7. The method of claim 6 wherein the input signals further include beam configuration request signals from the treatment rooms and a beam configuration signal from the accelerator and the comparing of the input signals verifies the authenticity of the requests from the selected treatment room.

8. The method of claim 7 further including using the beam configuration request signals to control the configuration of the beam from the accelerator.

9. The method of claim 8 wherein the input signals further include treatment room configuration signals.

10. The method of claim 7 wherein the input signals further include treatment room configuration signals.

11. The method of claim 6 further including using the treatment room beam request signals to control the beam path through the switchyard and the beam path configuration signal from the switchyard.

12. The method of claim 6 further comprising
  (d) denying beam transport to the selected treatment room in the absence of such verification.

13. The method of claim 6 further comprising generating a treatment room selection signal for the selected treatment room upon agreement of the beam request input signal from the selected one of the treatment rooms and the input signal from the switchyard and wherein the verification further comprises gating with the treatment room selection signal a plurality of treatment room configuration signals from the selected treatment room to beam controllers in the switchyard to control the transport of the beam to the selected treatment room.

* * * * *